United States Patent
Dair et al.

(10) Patent No.: US 6,843,788 B2
(45) Date of Patent: Jan. 18, 2005

(54) METHOD FOR USING A MASKING AGENT DURING LASER ABLATION

(75) Inventors: Geoffrey Thomas Dair, Subiaco (AU); Hank Christian Sciberras, Joondanna (AU); Sharon Lee Humphris, South Perth (AU)

(73) Assignee: Q-Vis Limited, Western Australia (AU)

( * ) Notice: Subject to any disclaimer, the term of this patent is extended or adjusted under 35 U.S.C. 154(b) by 59 days.

(21) Appl. No.: 10/124,445

(22) Filed: Apr. 17, 2002

(65) Prior Publication Data

US 2002/0183725 A1 Dec. 5, 2002

(30) Foreign Application Priority Data

Apr. 27, 2001 (AU) .............................................. PR4631

(51) Int. Cl.$^7$ ................................................. A61F 9/08
(52) U.S. Cl. ............................... 606/5; 606/2; 128/898
(58) Field of Search ...................... 606/2–19; 514/233.2

(56) References Cited

U.S. PATENT DOCUMENTS

| | | | | | |
|---|---|---|---|---|---|
| 4,968,454 A | * | 11/1990 | Crano et al. | ................. | 351/163 |
| 4,994,058 A | * | 2/1991 | Raven et al. | ................... | 606/5 |
| 5,021,196 A | * | 6/1991 | Crano et al. | ................. | 252/586 |
| 5,277,911 A | * | 1/1994 | Viegas et al. | .................... | 606/5 |
| 5,279,611 A | * | 1/1994 | McDonnell et al. | ............ | 606/4 |
| 5,324,281 A | * | 6/1994 | Muller | .......................... | 606/5 |
| 5,723,142 A | * | 3/1998 | Bowyer | .......................... | 606/5 |
| 6,080,144 A | * | 6/2000 | O'Donnell, Jr. | ................ | 606/5 |
| 6,399,107 B1 | * | 6/2002 | Kessler et al. | .............. | 424/646 |

* cited by examiner

*Primary Examiner*—Roy D. Gibson
*Assistant Examiner*—Henry M Johnson, III
(74) *Attorney, Agent, or Firm*—Baker Botts LLP

(57) ABSTRACT

A method of treating a surface by laser ablation to modify selected regions of the surface, while other regions of the surface not to be substantially ablated are protected from the laser beam by a masking fluid, wherein the masking fluid comprises a solution of a pharmaceutically acceptable pyrido benzoxazine compound or derivative thereof effective as a masking agent.

19 Claims, No Drawings

METHOD FOR USING A MASKING AGENT DURING LASER ABLATION

FIELD OF THE INVENTION

This invention relates generally to laser treatments that use a masking fluid for selectively mitigating the treatment in regions adjacent the desired treatment zone.

BACKGROUND ART

The clinical use of lasers has escalated in the last 20 years, in particular for treating diseases and disorders of the eye. Different wavelengths of laser light have been used to seal leaky retinal blood vessels, to remove debris from the posterior capsule of the lens after cataract surgery, and to correct refractive errors by reshaping the corneal stroma. The latter has proved to be an increasingly popular option for correction of refractive error compared to other means of refractive error correction such as contact lenses and spectacles. In addition to treating uniform refractive errors (myopia, hyperopia, astigmatism) laser vision correction technology has been used to treat corneal surface irregularities such as scars and various corneal dystrophies. This treatment of irregular corneal surface disorders is referred to as phototherapeutic keratectomy (PTK) and involves ablating a protruding region of cornea into a smoother surface.

In order to produce a uniform corneal surface by PTK the lower regions surrounding the protruding areas of cornea must be filled with a suitable medium, otherwise a uniform laser beam will simply ablate the current pattern further into the cornea. To provide such a medium, a masking fluid of high absorption (and therefore small penetration depth) and moderate viscosity is applied to the cornea, filling in the "valleys" and allowing uniform ablation of the cornea by the laser beam. This results in smoothing out of the irregular corneal surface. Masking fluids for laser refractive surgery using excimer lasers include balanced salt solution (BSS) and 0.9% saline solution.

Commercial laser refraction correction techniques have generally relied on the ultraviolet wavelength range and these have typically been developed using an excimer laser, which has been the mainstay of laser refractive surgery for several years. The excimer laser requires an argon-fluoride gas mixture as the optical media for the oscillation chamber. Although successful refractive error corrections have been made using the excimer laser, there are some problems that are associated with the use of gas as an optical medium. In addition, the gas requires continual replacement, which results in additional cost as well as a requirement for storage facilities.

These problems have been removed with the development of solid-state lasers, which use crystals as optical media instead of gas. Due to the different optical media used, there is a different wavelength emitted from the solid state laser (213 nm) compared to the excimer laser (193 nm). As a result, a larger penetration depth is potentially exhibited by the solid-state laser beam. As proposed in applicant's international patent publication WO 01/58398, this increased penetration depth is potentially advantageous as problems associated with excess fluid on the corneal surface during excimer laser surgery may be avoided when using a solid state laser. However, studies have shown that the same masking fluids used for excimer laser corrective surgery show markedly less light absorption when used for the same techniques using solid state lasers. This implies that these masking fluids are not suitable for PTK and another masking fluid is required if this procedure is to be executed using a solid-state laser.

SUMMARY OF THE INVENTION

It has been realised in accordance with the invention that certain pyrido benzoxazine compounds and derivatives are effective as masking agents in PTK and other laser treatments. An exemplary and effective masking agent is the derivative ofloxacin, an active ingredient of a commercial anti-bacterial solution used for treatment of the eye.

In accordance with a first aspect of the invention, there is provided a method of treating a surface by laser ablation to modify selected regions of the surface, while other regions of the surface not to be substantially ablated are protected from the laser beam by a masking fluid, wherein the masking fluid comprises a solution of a pharmaceutically acceptable pyrido benzoxazine compound or derivative thereof effective as a masking agent.

The wavelength of the laser beam utilised for the treatment is preferably 213 nm.

An effective such derivative, especially for a laser beam of 213 nm, is ofloxacin, the active component of the commercially available anti-bacterial solution Ocuflox (Trade Mark). Ofloxacin is of chemical formula $C_{18}H_{20}FN_3O_4$, has a molecular weight of 316.37, and has the chemical name 9-fluoro-2,3-dihydro-3-methyl-10-(4-methyl-1-piperazinyl)-7-oxo-7H-pyrido[1,2,3-de][1,4]benzoxazine-6-carboxylic acid.

More generally, the preferred class of masking agents are pyrido [1,2,3-de] [1,4] benzoxazine derivatives having the formula:

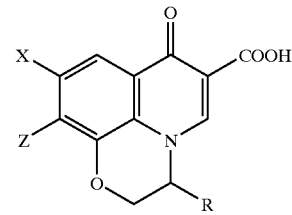

wherein X is a halogen atom, R is a hydrogen atom or an alkyl group having from 1 to 6 carbon atoms and Z represents (1) a mono-alkylamino or di-alkylamino group or (2) a cyclicamino group selected from the group consisting of azetidinyl, pyrrolidinyl, piperdinyl, morpholinyl, piperidinyl, homopiperazinyl, thiamorpholinyl and pyrazolidinyl, each of which amino groups may be substituted with a hydroxyl group, an alkyl group having 1 to 6 carbon atoms, an amino group, a hydroxyalkyl group having 1 to 6 carbon atoms or a mono- or di-alkylamino group having 1 to 6 carbon atoms in each alkyl group.

More generally, effective masking agents comprise pyrido benzoxazine compounds and derivatives as aforedescribed having a structural element effective to adequately absorb the laser beam wavelength to an extent sufficient for the compound to be a masking agent.

Preferably, the laser beam employed in the treatment is produced from a solid state laser, eg. a neodymium:YAG laser, and may typically be a selected harmonic of the fundamental laser wavelength produced by frequency conversion by suitable crystals.

A method to which the invention is advantageously applied is photottherapeutic keratectomy (PTK).

It is now proposed to describe the results by which ofloxacin was established as an effective masking agent for 213 nm laser beam. Light absorbent studies were carried out using 213 nm radiation produced as the fifth harmonic wavelength of the fundamental 1064 nm wavelength of an Nd:YAG laser, with a pulse duration of 6 ns and repetition rate of 20 Hz. The pulse energy of the laser was monitored using an energy detector and a storage oscilloscope. The energy of the laser was obtained from the amplitude of the voltage signal delivered from the detector.

Beer's Law states that if light is passed through solution, energy is attenuated according to the formula:

$$E_f = E_i e^{-\alpha_M C d}$$

Where: $\alpha_M$ is the molar absorption coefficient in $M^{-1}$ $cm^{-1}$

C is the concentration in moles per liter d is the distance in cm $E_f$ and $E_i$ are the final and initial pulse energies respectively.

In order to determine the amount of light absorbed (A) by the solution the molar absorption co-efficient is found from the gradient of the log-linear plot of Beer's law.

The absorption coefficient ($\alpha$ $cm^{-1}$) can then be calculated by multiplying the molar absorption coefficient by the concentration. Once the absorption coefficient is obtained, the penetration depth can be calculated from the reciprocal of this value. The penetration depth (in cm) can be used to determine whether the solution will provide enough absorbence to be used successfully in a PTK procedure using the 213 nm wavelength.

Ofloxacin is present in the ophthalmic solution Ocuflox (Trade Mark) at a concentration of 3 mg/ml. Measurements were then taken for ofloxacin at dilutions (in purified water) of the regular concentration; 1/100, 1/150, 1/200, 1/300, 1/500, 1/750, 1/1000. Readings were taken for BSS maintaining the same dilutions. By keeping the distance (or depth) constant and by varying the concentration a plot of transmission vs. concentration can be obtained as described previously. Five random readings were taken for each dilution and the mean calculated, in order to reduce the error from inter-pulse variations.

All data was obtained consecutively using the same laser to control for any variation between different lasers. Transmission for BSS and ofloxacin solution decreased exponentially with increasing concentration. These transmission plots were obtained for BSS and ofloxacin solutions using identical dilutions. There were no significant differences in intra-dilution energy readings.

Data obtained for ofloxacin solution and BSS were plotted and the log-linear plot of this data used to obtain the absorption coefficient. The data obtained for ofloxacin and BSS both fitted well to an exponential curve (R2=0.9806 and 0.9924 respectively). Ofloxacin exhibited a smaller penetration distance than BSS at the 213 nm wavelength and was comparable to BSS at the 193 nm wavelength (Table 1). BSS showed a noticeable increase in penetration distance using the 213 nm wavelength compared to its absorption in the 193 nm wavelength (Table 1).

TABLE 1

| Solution | $\alpha$ ($cm^{-1}$) | Penetration Depth ($\mu$m) |
|---|---|---|
| Ofloxacin (as Ocuflox ™) 213 nm | 198.6 | 50.3 |
| BSS (as Eye Stream ™) 193 nm | 140 | 72 |
| BSS (as Eye Stream ™) 213 nm | 12.42 | 805 |

The results from this study suggest that ofloxacin has masking properties that are ideal for use with the 213 nm solid-state laser. When compared to BSS at 213 nm, ofloxacin provides a penetration distance that is an order of magnitude shorter. These studies also confirm that BSS does not have the ability to mask 213 nm light sufficiently for PTK.

In addition, the similar penetration distance to BSS at 193 nm suggests that ofloxacin at 213 nm is just as suitable for use as a masking fluid. An essential property of a masking fluid is the ability to absorb the relevant laser light well, which is provided by ofloxacin but not BSS at the 213 nm wavelength. This absorption is essential for the fluid to shield deeper areas of cornea from ablation whilst the corneal protuberance is ablated.

Ofloxacin administered as Ocuflox solution has previously been used with the eye as an anti-bacterial agent and thus is known to have high biocompatibility, can be used for prolonged periods of time, and is readily available to clinicians. The realisation of the present invention that pyrido benzoxazine compounds such as ofloxacin are suitable as masking agents in laser ablation procedures on the eye appears therefore to be an especially convenient outcome. It is further known that the amount of ofloxacin absorbed by the surrounding tissues, as with most topical eye treatments, is a small percentage of the total drug delivered. The small amount of the compound actually absorbed by the cornea suggests that it may be suitable in larger concentrations in a PTK operation.

Ofloxacin fluoresces when the laser beam is incident on it, thus revealing whether the location of incidence is masked or otherwise. This would be a useful property in PTK.

In a second aspect, the invention provides a method of treating a surface by laser ablation with a 213 nm laser beam to modify selected regions of the surface, while other regions of the surface not to be substantially ablated are protected from the laser beam by a masking fluid, wherein the masking fluid comprises a solution of a pharmaceutically acceptable substance having the structural element of ofloxacin that makes it effective as a masking agent for a laser beam of 213 nm.

In a third aspect, the invention provides a pharmaceutically acceptable pyrido benzoxazine compound when used as a masking agent in the treatment of a surface by laser ablation to modify selected regions of the surface while other regions of the surface not to be substantially ablated are protected from the laser beam by the masking agent.

The invention further provides the use of a pharmaceutically acceptable pyrido benzoxazine compound as a masking agent in the treatment of a surface by laser ablation to modify selected regions of the surface while other regions of the surface not to be substantially ablated are protected from the laser beam by the masking agent.

What is claimed is:

1. A method of treating a surface by laser ablation with a laser beam to modify selected regions of the surface, comprising:

applying to other regions of the surface not to be substantially ablated a masking fluid that comprises a solution of a compound selected from pharmaceutically acceptable pyrido benzoxazine compounds and derivatives thereof effective as a masking agent for said laser beam; and directing said laser beam onto said surface to modify said selected regions by laser ablation, said other regions being protected from the laser beam by said masking fluid thereon.

2. A method according to claim 1 wherein the laser beam utilised for the treatment is of wavelength about 213 nm.

3. A method according to claim 2 wherein said solution is of a pharmaceutically acceptable pyrido benzoxazine compound or derivative having a structural element effective to adequately absorb the laser beam wavelength to an extent sufficient for the compound to be a masking agent.

4. A method according to claim 3, wherein the laser beam employed in the treatment is produced from a solid state laser, being a selected harmonic of the fundamental laser wavelength produced by frequency conversion by suitable crystals.

5. A method according to claim 2 wherein said masking fluid is a solution of one or more pyrido [1,2,3-de] [1,4] benzoxazine derivatives effective as a masking agent and having the formula:

wherein X is a halogen atom, R is a hydrogen atom or an alkyl group having from 1 to 6 carbon atoms and Z represents (1) a mono-alkylamino or di-alkylamino group or (2) a cyclic amino group selected from the group consisting of azetidinyl, pyrrolidinyl, piperdinyl, morpholinyl, piperidinyl, homopiperazinyl, thiamorpholinyl and pyrazolidinyl, each of which amino groups may be substituted with a hydroxyl group, an alkyl group having 1 to 6 carbon atoms, an amino group, a hydroxyalkyl group having 1 to 6 carbon atoms or a mono- or di-alkylamino group having 1 to 6 carbon atoms in each alkyl group.

6. A method according to claim 5 wherein said masking fluid is a solution of ofloxacin.

7. A method according to claim 6, wherein the laser beam employed in the treatment is produced from a solid state laser, being a selected harmonic of the fundamental laser wavelength produced by frequency conversion by suitable crystals.

8. A method according to claim 5, wherein the laser beam employed in the treatment is produced from a solid state laser, being a selected harmonic of the fundamental laser wavelength produced by frequency conversion by suitable crystals.

9. A method according to claim 2, wherein the laser beam employed in the treatment is produced from a solid state laser, being a selected harmonic of the fundamental laser wavelength produced by frequency conversion by suitable crystals.

10. A method according to claim 2, wherein said treatment is phototherapeutic keratectomy (PTK).

11. A method according to claim 2 wherein said masking solution fluoresces when the laser beam is incident on it.

12. A method according to claim 1 wherein said solution is of a pharmaceutically acceptable pyrido benzoxazine compound or derivative having a structural element effective to adequately absorb the laser beam wavelength to an extent sufficient for the compound to be a masking agent.

13. A method according to claim 1 wherein said masking fluid is a solution of one or more pyrido [1,2,3-de] [1,4] benzoxazine derivatives effective as a masking agent and having the formula:

wherein X is a halogen atom, R is a hydrogen atom or an alkyl group having from 1 to 6 carbon atoms and Z represent (1) a mono-alkylamino or di-alkylamino group or (2) a cyclicamino group selected from the group consisting of azetidinyl, pyrroddlidinyl, piperdinyl, morpholinyl, piperidinyl, homopiperazinyl, thiamorpholinyl and pyrazolidinyl, each of which amino groups may be substituted with a hydroxyl group, an alkyl group having 1 to 6 carbon atoms, an amino group, a hydroxyalkyl group having 1 to 6 carbon atoms or a mono- or di-alkylamino group having 1 to 6 carbon atoms in each alkyl group.

14. A method according to claim 13 wherein said masking fluid is a solution of ofloxacin.

15. A method of treating a surface by laser ablation with a 213 nm laser beam to modify selected regions of the surface, comprising:

applying to other regions of the surface not to be substantially ablated a masking fluid that comprises a solution of a compound selected from pharmaceutically acceptable substances having a structural element of ofloxacin that makes it effective as a masking agent for a laser beam of 213 nm; and directing said laser beam onto said surface to modify said selected regions by laser ablation, said other regions being protected from the laser beam by said masking fluid thereon.

16. A method according to claim 15, wherein the laser beam employed in the treatment is produced from a solid state laser, being a selected harmonic of the fundamental laser wavelength produced by frequency conversion by suitable crystals.

17. A method according to claim 16 wherein said treatment is phototherapeutic keratectomy (PTK).

18. A method according to claim 15 wherein said treatment is phototherapeutic keratectomy (PTK).

19. A method according to claim 15 wherein said masking solution fluoresces when the laser beam is incident on it.

* * * * *